United States Patent [19]

Hutchison et al.

[11] 4,149,420
[45] Apr. 17, 1979

[54] ULTRASONIC PHASED ARRAY SYSTEMS

[75] Inventors: James M. S. Hutchison; Robert D. Selbie, both of Aberdeen, Scotland

[73] Assignee: National Research Development Corporation, London, England

[21] Appl. No.: 848,522

[22] Filed: Nov. 4, 1977

[30] Foreign Application Priority Data

Nov. 4, 1976 [GB] United Kingdom ............... 45962/76

[51] Int. Cl.² ............................................... G01N 29/00
[52] U.S. Cl. ..................................... 73/626; 128/2 V; 340/5 MP
[58] Field of Search ................. 73/626, 628; 128/2 V, 128/2.05 Z; 340/1 R, 3 R, 5 MP

[56] References Cited

U.S. PATENT DOCUMENTS

| | | | |
|---|---|---|---|
| 3,881,466 | 5/1975 | Wilcox | 73/626 X |
| 3,918,024 | 11/1975 | Macovski | 73/626 X |
| 3,919,683 | 11/1975 | Itamura et al. | 73/626 X |
| 4,058,003 | 11/1977 | Macovski | 73/626 X |
| 4,064,741 | 12/1977 | Reynolds | 73/626 X |

Primary Examiner—Stephen A. Kreitman
Attorney, Agent, or Firm—Cushman, Darby & Cushman

[57] ABSTRACT

Ultrasonic phased array method and apparatus for the static or dynamic investigation of structures, such as organs of the body, or intra-uterine detail, wherein ultrasonic echo pulses, reflected back from a testpiece to one or a group of adjacent transducers of a linear transducer array, are converted to corresponding electric signals which are then processed to maximize the response to the echo pulses reflected from points on a predetermined axis and to minimize the response to all other echo pulses. The method is repeated using another group of transducers in the array and another predetermined axis to produce fields of video information which are focussed and then interlaced to provide an image of the testpiece at a particular instance, the method steps being repeated in rapid succession to provide a video image representative of the testpiece in real time.

3 Claims, 4 Drawing Figures

ULTRASONIC PHASED ARRAY SYSTEMS

This invention relates to a method and apparatus for use in the static or dynamic investigation of moving structures, organs of the body, such as the heart, or intra-uterine detail using ultrasonic imaging techniques in real time, such methods and apparatus being known as ultrasonic phased array, scanned array or sequentially switched systems.

As disclosed in an article by Bom et al entitled "Ultrasonic Viewer for Cross-Sectional Analyses of Moving Cardiac Structures", known ultrasonic phased array systems used in the dynamic study of moving structures consists of a number of electro-acoustic or piezo-electric transducers arranged in the form of a linear array located on or adjacent, and ultrasonically coupled to, the structure or testpiece to be studied and imaged by scanning. One or a group of adjacent transducers in the array is pulsed electrically and thus transmits a pulse or pulses of ultrasonic energy into the testpiece. Echo pulses emanating from the testpiece are detected by the same transducer or group of adjacent transducers and the electrical signals thus generated are used to modulate the brightness of a video screen. The rectangular co-ordinates of the echo pulses thus produced are determined in depth into the testpiece from the surface of the linear array as the time lapse between the transmitted pulse and the detected echo pulse, and in the direction parallel to the line of the transducers in the array by the position of the transducer or group of transducers in the array. The procedure is repeated using subsequent transducers or groups of adjacent transducers until echo pulses from each transducer in the array have produced a brightness modulation on the corresponding area of the video screen. A complete set of such signals thus produced is termed a field of video information. One, or a number of such video information fields, may be interlaced to produce a picture or frame, the image thus produced being representative of a view of the testpiece, in the manner described, and this is referred to as a "B-scan".

The complete procedure is repeated rapidly and subsequent picture frames of static information give the impression of a moving picture which is the image representing a moving testpiece and which is referred to as a "dynamic B-scan". Such a system suffers from one disadvantage in that the specular echo signals are not focussed, thus limiting the resolution of the system.

An object of this invention is to provide a sequentially switched or phased array system in which the echo signals detected by a group of adjacent transducers are processed electronically such that a focussed image results in each area of the picture frame, thus enhancing the image of the testpiece, the system being referred to as a "Dynamic Phased Array".

Accordingly, one aspect of the invention provides a method of ultrasonically investigating a testpiece, which method comprises:

(a) locating a group of adjacent ultrasonic transducers in a linear array on or adjacent, and ultrasonically coupled to, a testpiece to be investigated;

(b) transmitting, from one or more transducers of said group, ultrasonic energy into the testpiece;

(c) receiving, in transducers in said group, ultrasonic echo pulses reflected from the testpiece;

(d) producing signals, in the form of electrical energy, corresponding to the received ultrasonic echo pulses;

(e) processing the electrical signals in such a way as to maximize the response to the echo pulses reflected from points on a predetermined axis, which is referred to as the "locus of swept focus" and is perpendicular to said group, and to minimize the response to all other echo pulses, this step being referred to as "dynamic or swept focussing";

(f) advancing along the linear array and selecting a further group of adjacent transducers and repeating steps (a) to (e) with the exception that a different predetermined axis is chosen in (e);

(g) repeating steps (a) to (f) until electrical signals from all groups of adjacent transducers in the linear array have been processed to form a field of video information as hereinbefore defined;

(h) repeating steps (a) to (g) with the exception that different axes are chosen in (e) to form further unique fields of video information;

(i) interlacing all the fields of video information to produce a picture or frame of information that is an image representative of the testpiece at a particular intant;

(j) repeating steps (a) to (i) in rapid succession such that successive pictures or frames of information are viewed as an image representative of the testpiece in real time A further aspect of the invention provides an apparatus for ultrasonically investigating a testpiece, which apparatus comprises a group of ultrasonic transducers locatable in a linear array on or adjacent, and arranged to be ultrasonically capable, in use, of transmitting ultrasonic energy into and receiving ultrasonic echo pulses from the testpiece; means for producing electrical signals corresponding to received ultrasonic echo pulses; means for processing said electrical signals to maximize the response to the echo pulses emanating from points on a predetermined axis perpendicular to said group and to minimize the response to all other echo pulses; means for selectively causing a number of adjacent transducers in said group to transmit ultrasonic energy into the testpiece; means for causing at least a further number of adjacent transducers in said group to transmit ultrasonic energy into the testpiece; means for processing the electrical signals produced from said first-mentioned processing means to provide fields of video information; means for interlacing said video information fields to provide an image representative of the testpiece at a particular instance; and means for combining successive images to produce an image representative of the testpiece in real time.

In order that the invention may be more fully understood, an ultrasonic phased array apparatus, in accordance therewith, for use in a method of investigating the human heart and intra-uterine detail will now be described by way of example and with reference to the accompanying drawings in which.

Figure 1:
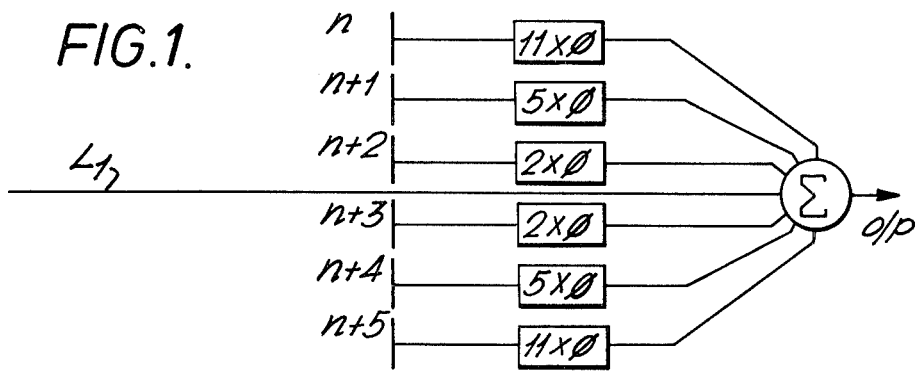
FIG. 1 is a diagrammatic representation of a group of six adjacent transducers in a linear array which generates an X field, with the nth transducer being odd or even.
Figure 2:
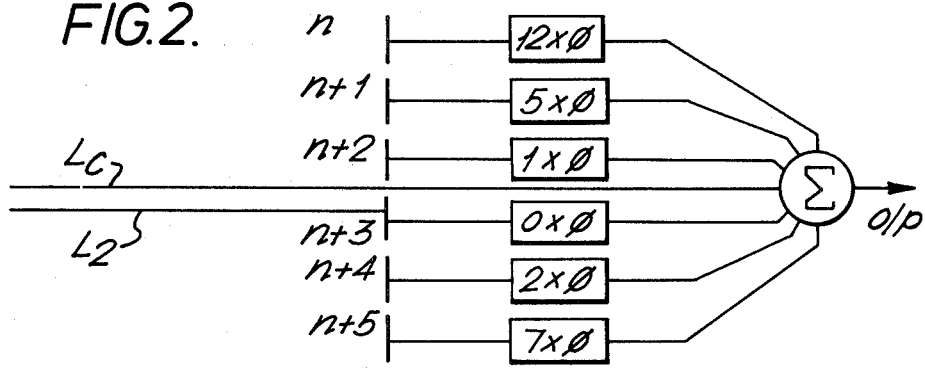
FIG. 2 is a diagrammatic representation of the group of six transducers, as shown in FIG. 1, which generates Y and Z fields, with the nth transducer being odd in the Y field and even in the Z field.
Figure 3:
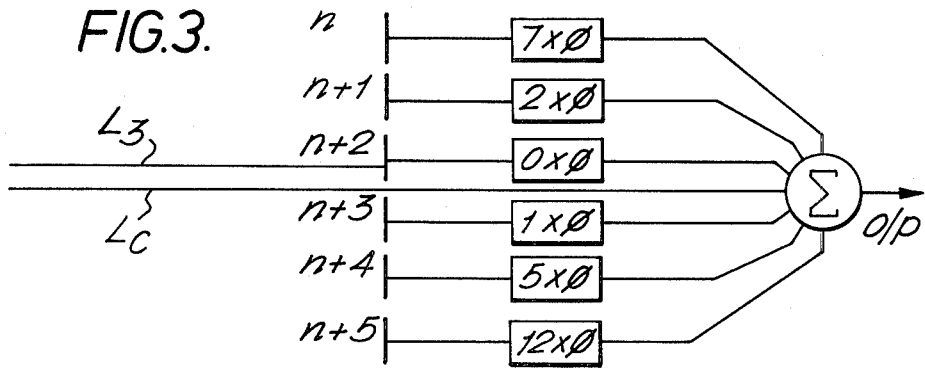
FIG. 3 is a diagrammatic representation of the group of transducers, as shown in FIG. 1, which generates Y and Z fields, with the nth transducer being even in the Y field and odd in the Z field.

In the system described below, a linear array of transducers was manufactured from one long piezo-electric transducer which was divided into 36 separate transducer elements. Referring to FIGS. 1 to 3, only one group of six such adjacent transducer elements, n to n+5, is described, although there are 31 groups of six adjacent elements in the array of 36 elements. The linear array of 36 transducer elements, which is placed adjacent and is ultrasonically coupled to a testpiece, for instance, on the surface of the human body adjacent the heart, to be investigated, transmits ultrasonic energy in the form of pulses and receives echo pulses, electrical signals being generated from the received echo pulses. These electrical signals are processed to form 3 interlaced fields, referred to as X, Y and Z, each having 31 lines of information to display a 93 line picture frame. The frames are repeated at a rate of 25 frames per second. For practical considerations, there are 32 lines generated per field but one line in each field, that is, 3 lines per frame, contain no signal information.

Considering, firstly the X field, then, during the recovery time or fly-back period at the end of the (n−1)th line, elements n+2 and n+3 are pulsed simultaneously by a transmitter and, during the nth line, elements n to n+5 are switched to circuitry which effectively focusses the electric signals generated from echo pulses emanating from an axis L perpendicular to the transducer element array and bisecting the group of 6 adjacent elements, as shown in FIG. 1. This axis L is referred to as the "locus of swept focus" and focus along it is achieved by introducing phase advances which are integer multiples of an angle $\phi$ to the elements n to n+5 as follows:

| element | phase advance |
|---|---|
| n and n+5 | $11 \times \phi$ |
| n+1 and n+4 | $5 \times \phi$ |
| n+2 and n+3 | $2 \times \phi$ |

The value of the angle $\phi$ decreases as a function of time in such a way that during the nth line a dynamic or swept focus is effected. The system is advanced by one element spacing along the transducer element array to a subsequent group of 6 adjacent elements and the procedure is repeated. The process is continued until the X field of 31 lines is complete.

Consider, secondly, the Y field. As before, during the fly-back period of the (n−1)th line, elements n+2 and n+3 are pulsed by the transmitter and during the nth line, elements n to n+5 are switched to circuitry which effectively focusses the electric signals generated from the echo pulses emanating from an axis $L_2$ normal to the transducer array. This time, if n is odd, then the locus of swept focus is displaced from the centre line $L_c$ by one-third of an element spacing towards the element n+3, as shown in FIG. 2. Focus along this axis $L_2$ is achieved by introducing phase advances which are integer multiples of the angle $\phi$ to the elements as follows:

| element | phase advance |
|---|---|
| n | $12 \times \phi$ |
| n+1 | $5 \times \phi$ |
| n+2 | $\phi$ |
| n+3 | no advance |
| n+4 | $2 \times \phi$ |
| n+5 | $7 \times \phi$ |

If n is even, then the locus of swept focus is displaced from the centre line by one-third of an element spacing towards the element n+2, as shown in FIG. 3. Focus along this axis $L_3$ is achieved by introducing phase advances to the elements as follows:

| element | phase advance |
|---|---|
| n | $7 \times \phi$ |
| n+1 | $2 \times \phi$ |
| n+2 | no advance |
| n+3 | $\phi$ |
| n+4 | $5 \times \phi$ |
| n+5 | $12 \times \phi$ |

As in the X field, the value of $\phi$ is the same decreasing function of time as the nth line is scanned and a swept focus is again effected. The system is advanced by one element spacing along the transducer element array to a subsequent group of six adjacent elements and the procedure is repeated. The process is continued until the Y field of 31 lines is complete.

Thirdly, in the Z field, the procedure is converse to that of the Y field. When n is odd, the locus of swept focus is displaced from the centre line $L_c$ by one-third of an element spacing towards the element n+2, as shown in FIG. 3. Focus along this axis $L_3$ is achieved by introducing phase advances to the elements as follows:

| element | phase advance |
|---|---|
| n | $7 \times \phi$ |
| n+1 | $2 \times \phi$ |
| n+2 | no advance |
| n+3 | $\phi$ |
| n+4 | $5 \times \phi$ |
| n+5 | $12 \times \phi$ |

When n is even, the locus of swept focus is displaced by one-third of an element spacing towards the element n+3, as shown in FIG. 2. Focus along this axis $L_2$ is achieved by introducing phase advances to the elements as follows:

| element | phase advance |
|---|---|
| n | $12 \times \phi$ |
| n+1 | $5 \times \phi$ |
| n+2 | $\phi$ |
| n+3 | no advance |
| n+4 | $2 \times \phi$ |
| n+5 | $7 \times \phi$ |

The three fields, which are individually unique in signal content, cycle in the order X, Y and Z and are interlaced to give a 93 line picture frame where the echo signals at any point on the video display are "in focus".

In each case, the echo signals are not processed directly but by an indirect method which is similar to the method described by Voglis in Ultrasonics 9 pages 142–153 and 215–223 (1971).

Figure 4:
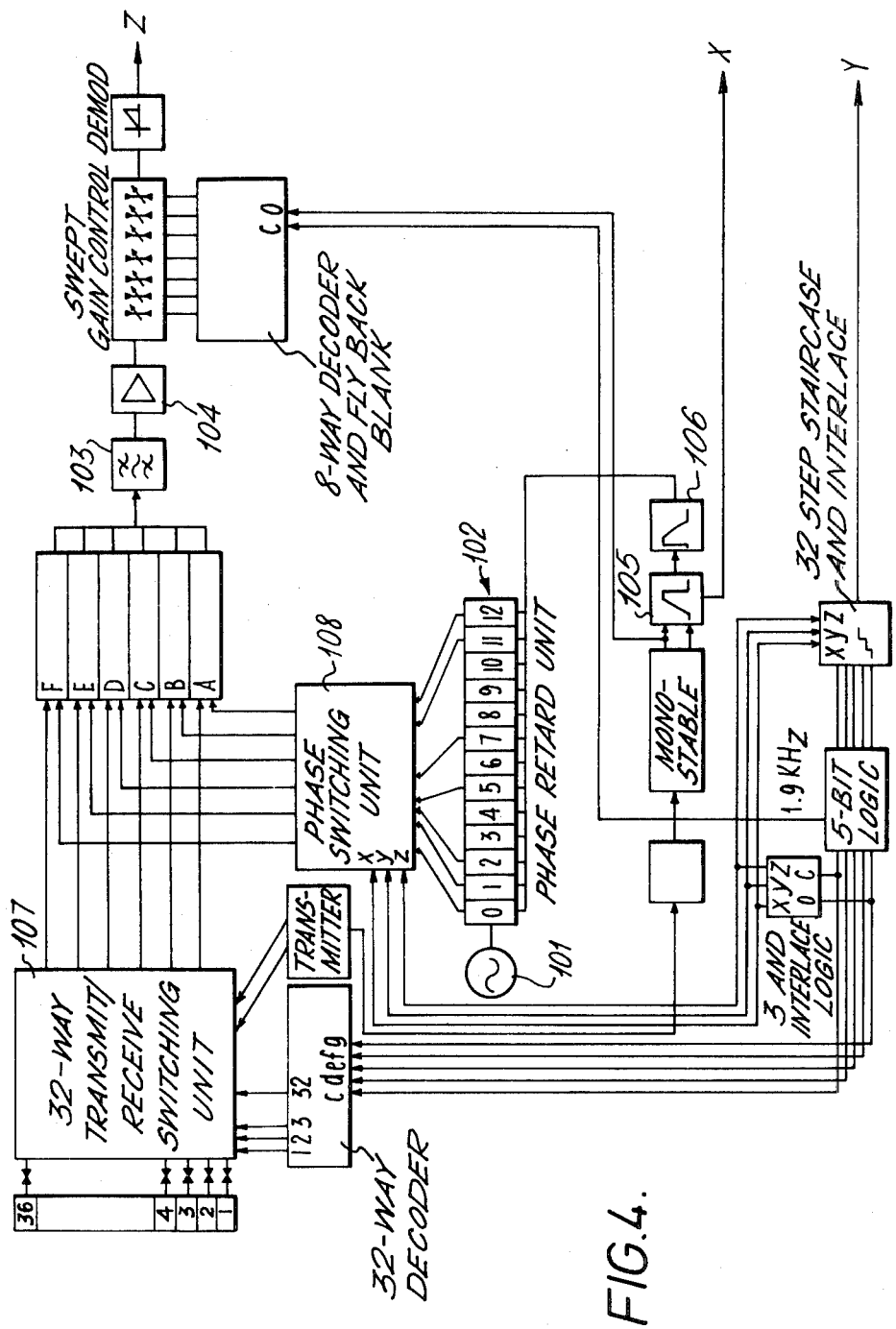
FIG. 4 is a block schematic diagram of electronic processing apparatus incorporating the transducer groups of FIGS. 1, 2 and 3.

The electrical echo signals from the transducer elements 1 to 36 may be considered as a damped oscillation of a few cycles at 2 MHz. A local oscillator 101 of 4 MHz, or thereabouts, drives a cascade 102 of 12 phase retard networks each retarding the phase of the reference phase of the local oscillator by a phase angle $\phi$, as shown in FIG. 4. Suitable logic is generated to switch the signals from the six adjacent transducer elements, via a 32-way transmit/receive switching unit 107, and six of the 13 phases to six balanced modulators, via a phase switching unit 108, the modulators being referred to as A, B, C, D, E and F as follows:

During the nth line of the X field.

| (n odd) | (n even) | phase | balanced modulator |
|---------|----------|-------|--------------------|
| n       | n+5      | 11 × $\phi$ | A |
| n+1     | n+4      | 5 × $\phi$  | B |
| n+2     | n+3      | 2 × $\phi$  | C |
| n+3     | n+2      | 2 × $\phi$  | D |
| n+4     | n+1      | 5 × $\phi$  | E |
| n+5     | n        | 11 × $\phi$ | F |

During the nth line of the Y and Z fields.

| element | | phase | balanced modulators |
|---------|---|-------|---------------------|
| [Y field: (n odd) (n even)] | | | |
| [Z field: (n even) (n odd)] | | | |
| n       | n+5 | 12 × $\phi$ | A |
| n+1     | n+4 | 5 × $\phi$  | B |
| n+2     | n+3 | 1 × $\phi$  | C |
| n+3     | n+2 | 0 (reference phase) | D |
| n+4     | n+1 | 2 × $\phi$  | E |
| n+5     | n   | 7 × $\phi$  | F |

The outputs of the 6 balanced modulators A to F contain only the lower side frequency components and the upper side frequency components of the local oscillator 101 modulated by the echo signals, the local oscillator frequency being suppressed. A band pass filter 103 substantially rejects the upper side frequency components of the modulated signal and any vestige of the local oscillator frequency allowing only the lower side frequency components to pass unattended. The lower side frequency components are at a frequency which is the difference between the local oscillator frequency and the echo signal or transducer element frequency. Since the local oscillator frequency is higher than the transducer element signal frequency, the lower side frequency component is advanced in phase by the same angle as the local oscillator frequency is retarded in phase. The lower side frequency components, each advanced by the appropriate integer multiple of the phase angle $\phi$, are summed to produce a composite signal and will be cumulative if the echo signals emanate from the locus of swept focus but, otherwise, appear as a lower level noise. Thus the system is dynamically focussed. The composite signal is amplified in an amplifier 104 and converted to modulate the brightness of a video display according to its amplitude.

The 12 phase retard networks 102 are indirectly controlled by the ramp functions of 105, 106 of the line scan of the video display in such a way that the value of $\phi$ is decreased inversely with time during the line scan in order to sweep the focus.

The gain control of the amplifier 104 is time dependent such that it is possible to manually adjust the gain contour in 7 steps. Thus, the amplification of signals received from the different depths of tissue can be varied to maximize picture detail consistent with prevailing conditions.

We claim:

1. A method of ultrasonically investigating a testpiece, which method comprises the steps of:
   (a) locating a group of adjacent ultrasonic transducers in a linear array adjacent, and ultrasonically coupled to, said testpiece;
   (b) transmitting from one or more transducers of said group, ultrasonic energy into said testpiece;
   (c) receiving, in transducers in said group, ultrasonic echo pulses reflected from said testpiece;
   (d) producing signals, in the form of electrical energy, corresponding to the received ultrasonic echo pulses;
   (e) separately amplitude modulating said electrical signals with separate phases of a carrier wave, the separate phases of the carrier wave being integral multiples of a phase angle;
   (f) varying the phase angle inversely with time to maximize the response of the group of transducer elements along a predetermined axis within the testpiece and perpendicular to said group;
   (g) changing the integer multiples of the phase angle to maximize the response of the group of transducer elements along other predetermined axes within the testpiece and perpendicular to said group;
   (h) summing the lower side frequencies of the separate amplitude modulated carrier waves to produce video signals which correspond to ultrasonic echoes from along the predetermined axes;
   (i) selecting another group of adjacent transducer elements in said linear array and repeating the first mentioned processes to maximize the response of the group along other predetermined axes and to produce video signals which correspond to ultrasonic echoes from along these predetermined axes;
   (j) continuing the aforementioned processes; and
   (k) processing the video signals to produce an image on an equally spaced line raster on a screen representative of the testpiece in real time.

2. An apparatus for ultrasonically investigating a moving testpiece, which apparatus comprises:
   a selected group of adjacent transducer elements located in a linear array of transducer elements adjacent, and ultrasonically coupled to, said testpiece, some of said transducer elements in said group periodically transmitting ultrasonic energy into said testpiece, each of the transducer elements in said group periodically receiving separately ultrasonic echo pulses from said testpiece;
   means for producing separate electrical signals corresponding to the received ultrasonic echo pulses;
   means for separately amplitude modulating said electrical signals with separate phases of a carrier wave, the separate phases of the carrier wave being integer multiples of a phase angle;
   means for varying the phase angle inversely with time to maximize the response of the group of transducer elements along a predetermined axis within the testpiece and perpendicular to said group;
   means for changing the integer multiples of the phase angle to maximize the response of the group of transducer elements along other predetermined axes within the testpiece and perpendicular to said group;

means for summing the lower side frequencies of the separate amplitude modulated carrier waves to produce video signals which correspond to ultrasonic echoes from along the predetermined axes;

means for selecting another group of adjacent transducer elements in said linear array and repeating the first mentioned processes to maximize the response of the group along other predetermined axes and to produce video signals which correspond to ultrasonic-echoes from along these predetermined axes;

means for continuing the aforementioned processes; and means of processing the video signals to produce an image on an equally spaced line raster on a screen representative of the testpiece in real time.

3. An apparatus as claimed in claim 2, in which said first-mentioned processing means comprises a balanced modulator, in which the frequencies of the electrical signals are modulated by a known frequency that is greater than said electrical signal frequencies, prior to modulation, and a band pass filter which rejects the upper side frequency components so-produced and the known frequency to produce lower side frequency components having a frequency which is equal to the difference between the known frequency and the electrical signal frequencies, prior to modulation.

* * * * *